United States Patent [19]

Kasahara et al.

[11] Patent Number: 5,161,521
[45] Date of Patent: Nov. 10, 1992

[54] OSCILLATION DEGREE MEASURING APPARATUS

[75] Inventors: Yoichi Kasahara; Hisatsune Kadota, both of Machida; Norio Kaneko, Yokohama, all of Japan

[73] Assignee: Nikon Corporation, Tokyo, Japan

[21] Appl. No.: 603,621

[22] Filed: Oct. 26, 1990

[30] Foreign Application Priority Data

Nov. 6, 1989 [JP] Japan .................................. 1-288094

[51] Int. Cl.$^5$ ............................................. A61B 17/60
[52] U.S. Cl. ........................... 128/24 AA; 128/660.01; 604/22; 73/573; 73/576; 73/579; 73/602
[58] Field of Search .......... 604/22; 128/24 A, 660.01; 73/573-575, 577, 579, 588, 602

[56] References Cited

U.S. PATENT DOCUMENTS

| | | | |
|---|---|---|---|
| 4,383,446 | 5/1983 | Roeder et al. | 73/579 |
| 4,502,329 | 3/1985 | Fukunaga et al. | 73/573 |
| 4,543,827 | 10/1985 | Tominaga et al. | 73/602 |

FOREIGN PATENT DOCUMENTS 0292553 12/1986 Japan .

Primary Examiner—David M. Shay
Attorney, Agent, or Firm—Shapiro and Shapiro

[57] ABSTRACT

An oscillation degree measuring apparatus measures the fixing state of an object to be measured as a numerical value of the degree of oscillation and comprises an ultrasonic exciter for generating ultrasonic waves which shock the object and exciting oscillations, an oscillation detector for detecting the oscillations of the object and converting the oscillations into electrical signals, a band amplifier for extracting a signal element of a predetermined frequency band including a resonant frequency of the object from the detected signals from the oscillation detector, a smoothing circuit for smoothing the signals amplified by the band amplifier, an A/D converter for converting the signals smoothed by the smoothing circuit into digital signals, a control device for operating the A/D converter a plurality of times every time a predetermined time passes, and a data processor for finding an average value of a plurality of digital data obtained by the A/D converter and calculating the degree of oscillation based on the average value.

4 Claims, 5 Drawing Sheets

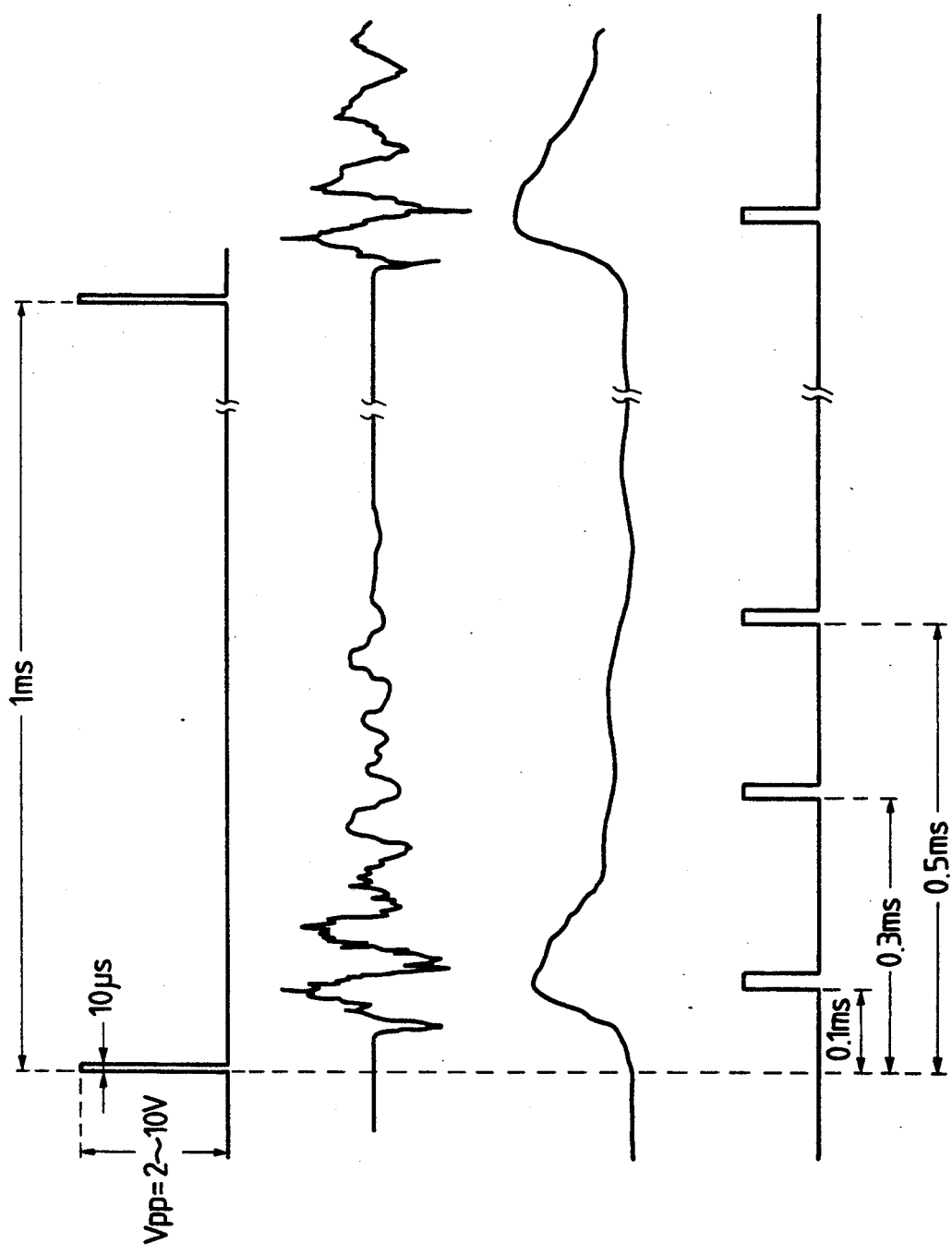

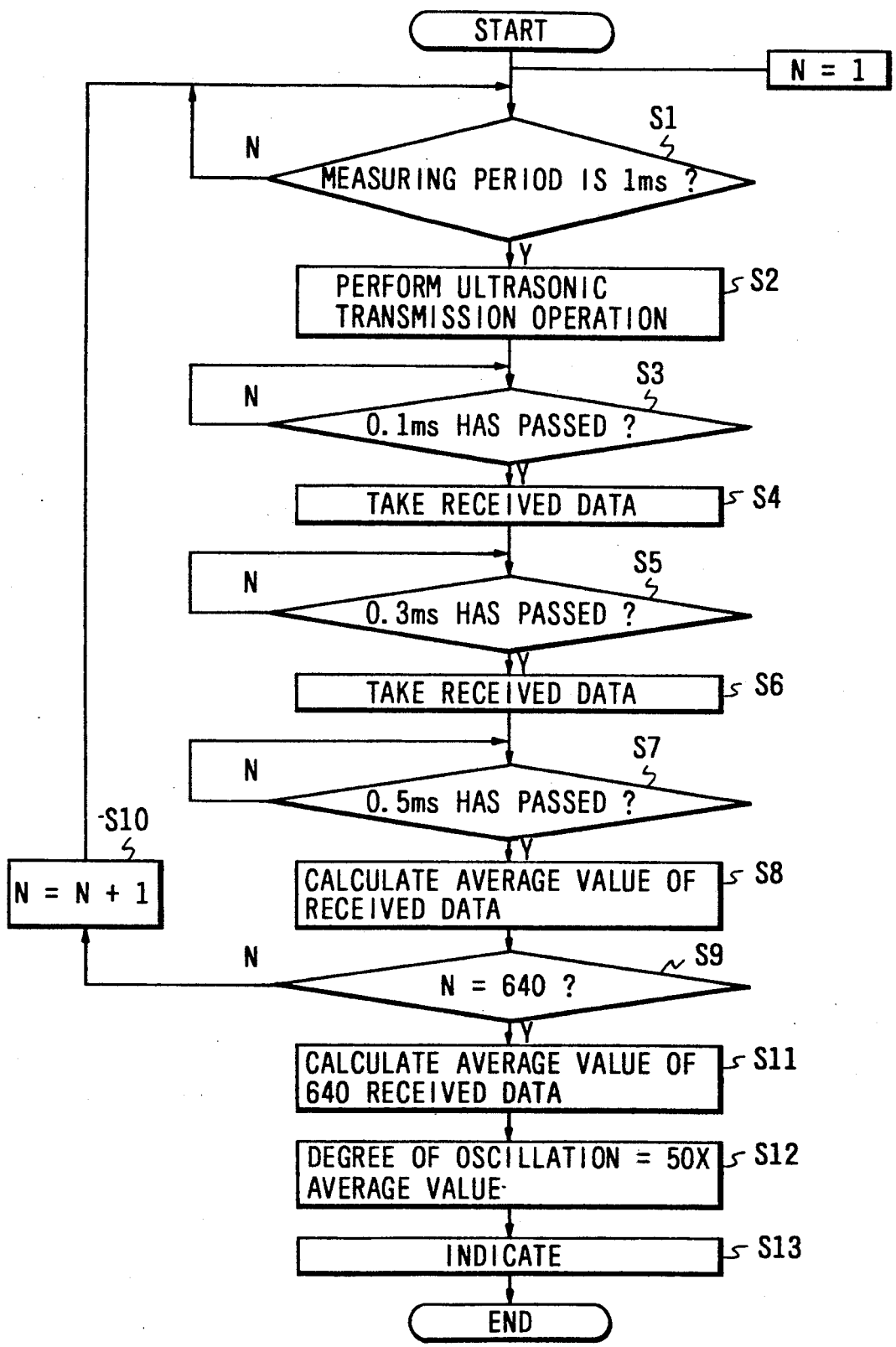

OSCILLATION DEGREE MEASURING APPARATUS

BACKGROUND OF THE INVENTION

1. Field of the Invention

The present invention relates to a measuring apparatus for inspecting a fixing state of an object to a supporting member, and more particularly to an oscillation degree measuring apparatus for inspecting a fixing state of a small object, such as the root of a tooth.

2. Related Background Art

A dental implant (the root of a tooth) is given as an example of an object whose fixing state is required to be measured. The fixing state can be thought of as the degree of oscillation of an object to be measured. The degree of oscillation means the amount of oscillation of the object to be measured when a certain shock is given to the object.

In general, if a natural tooth is lost due to a cavity in the tooth or by an accident, since the root of the tooth for supporting the crown is also lost, a treatment using a bridge or the like is performed. However, the bridge causes an excessive burden on the natural supporting teeth on both sides of the bridge, and shortens the lives of such supporting teeth.

In order to solve the above problem, a treatment which buries and fixes an implant for supporting the crown of a tooth in a jaw bone and mounts an artificial crown thereon has been studied, and many implants are now in practical use. When a certain kind of implant is used, it is necessary to measure the fixing state of the implant in an operation. For example, in the case of an implant which is directly joined with a jaw bone, if the implant is insufficiently buried and fixed in the jaw bone, soft tissue intrudes between the implant and the jaw bone, and the implant cannot be directly joined with the jaw bone and cannot effectively function. Therefore, it is essential to confirm that the implant is sufficiently fixed when it is buried.

However, it is difficult to measure the fixing state of the implant in a conventional measurement method. In other words, except for the case in which soft tissue between the implant and the jaw bone develops extremely thick, it is difficult to diagnose an insufficient fixing by a general X ray, and an X-ray image gives only information as to the vicinity of an outline of the implant. On the other hand, a measurement method which applies a strong force to the implant is likely to break the fixing state which has been obtained.

The inventors of the present invention invented an apparatus for measuring slight oscillations of an implant by ultrasonic waves and diagnosing the fixing state of the implant, which has been already disclosed in Japanese Patent Application Laid-open No. 60-190941.

The disclosed apparatus transmits ultrasonic oscillations, which are generated from an ultrasonic oscillation source and include at least a predetermined resonant frequency element, to an implant buried in a jaw bone through an ultrasonic wave transmitting means, detects the oscillations excited by the implant by a detection means, converts a resonant phenomenon at the above predetermined resonant frequency into electrical signals and observes the electrical signals, and diagnoses the fixing state of the implant based on whether or not the resonant phenomenon is present.

However, in such a conventional apparatus which observes ultrasonic oscillations, since electrical signals representative of the oscillations of the implant are observed by an oscilloscope, the oscillation waveforms include much information while they include unnecessary information, and a processing method of received signals is not sufficiently established, it is difficult to objectively judge numerical values of the degree of oscillation representing the fixing state and to aptly evaluate the fixing state.

SUMMARY OF THE INVENTION

It is an object of the present invention to provide an oscillation degree measuring apparatus which can solve such a conventional problem, extract necessary information from detected oscillation information of an object to be measured, and find the degree of oscillation of the object to be measured as a numerical value.

In order to achieve the above object, an oscillation degree measuring apparatus of the present invention comprises an ultrasonic exciting means for generating ultrasonic waves which shock an object to be measured and exciting oscillations, an oscillation detection means for detecting the oscillations of the object to be measured and converting the oscillations into electrical signals, a band amplifying means for extracting a signal element of a predetermined frequency band including a resonant frequency of the object to be measured from the detected signals from the oscillation detection means, a smoothing circuit means for smoothing the signals amplified by the band amplifying means, an A/D converter means for converting the signals smoothed by the smoothing circuit means into digital signals, a control means for operating the A/D converter means a plurality of times every time a predetermined time passes, and a data processing means for finding an average value of a plurality of digital data obtained by the A/D converter means and calculating the degree of oscillation based on the average value.

According to the above structure, the oscillation degree measuring apparatus of the present invention can measure the fixing state of a small object, for example, a buried dental implant, as a numerical value of the degree of oscillation and simply and precisely judge and evaluate the fixing state of the buried small object.

Other objects, features and advantages of the present invention will be sufficiently apparent from the following detailed description in connection with the accompanying drawings.

BRIEF DESCRIPTION OF THE DRAWINGS

FIGS. 4A to 4D are time charts explaining operations of the embodiment shown in FIG. 3;

FIG. 5 is an operational flowchart showing measurement processes by the embodiment shown in FIG. 3.

DETAILED DESCRIPTION OF THE PREFERRED EMBODIMENTS

The preferred embodiments of the present invention will now be described with reference to the accompanying drawings.

Figure 1:
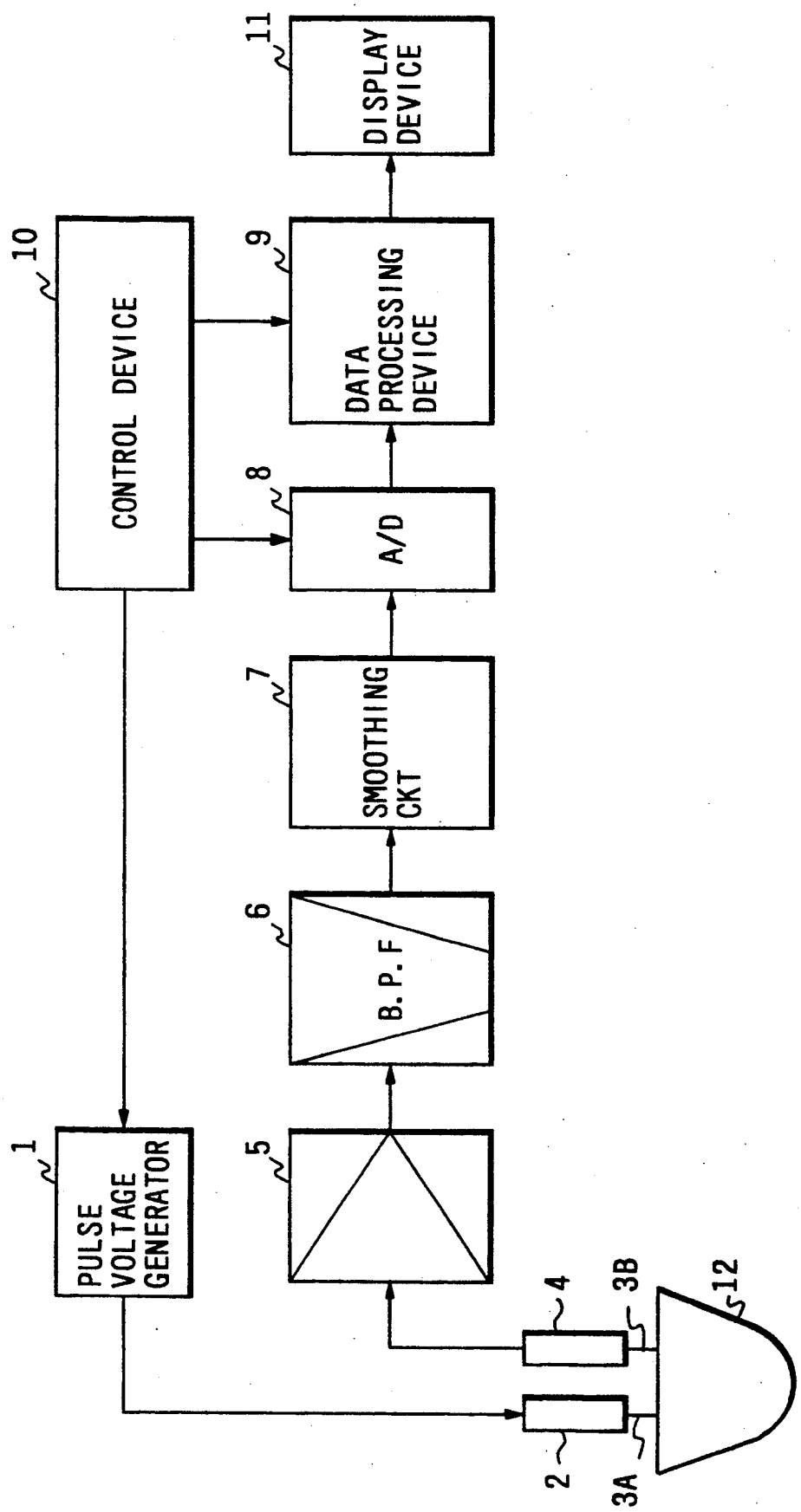
FIG. 1 is a block diagram showing the composition of an oscillation degree measuring apparatus of the present invention.

FIG. 1 is a block diagram schematically showing the composition of an oscillation degree measuring apparatus of the present invention The oscillation degree measuring apparatus comprises an ultrasonic exciting means composed of a pulse voltage generator 1 for transmitting ultrasonic oscillations to an object 12 to be measured through an oscillation transmitting member 3A and exciting the oscillations and an ultrasonic oscillator 2, and an oscillation detection means including an ultrasonic explorer 4 for detecting the oscillations of the object 12 to be measured through an oscillation transmitting means 3B and converting the detected oscillations into electrical signals, in the same manner as the apparatus disclosed in Japanese Patent Application Laid-open No. 60-190941.

In order to find the degree of oscillation from the signals obtained by the oscillation detection means, the apparatus of the present invention further comprises a band amplifying means composed of an amplifier 5 for extracting a signal element of a predetermined frequency band including a resonant frequency of the object 12 to be measured from the signals obtained by the oscillation detection means and a band pass filter 6, a smoothing means including a smoothing circuit 7 for smoothing the signals amplified by the band amplifying means, an A/D converter means including an A/D converter 8 for converting the signals smoothed by the smoothing means into digital signals, a control means including a control device 10 for operating the A/D converter means a plurality of times every time a predetermined time passes and a data processing means including a data processing device 9 for finding an average value of a plurality of digital data obtained by the A/D converter means, calculating the degree of oscillation based on the average value and displaying the degree of oscillation in a display means including a display device 11.

Operations of the oscillation degree measuring apparatus of the present invention having such a composition are as follows.

Ultrasonic oscillations including a resonant frequency of the object 12 to be measured are generated by the excitement of the ultrasonic oscillator 2 by electrical pulse signals generated by the pulse voltage generator 1, and the object 12 to be measured, such as a dental implant, is resonated through the oscillation transmitting member 3A. The oscillations of the object 12 are transmitted to the ultrasonic explorer 4 through the oscillation transmitting member 3B, converted into electrical signals by the ultrasonic explorer 4 and detected. The detected signals from the ultrasonic explorer 4 amplified by the amplifier 5 and only a signal element of a predetermined frequency band including a resonant frequency of the object 12 is taken out by the band pass filter 6. The band of the band pass filter 6 is determined by the state of an object to be measured and so on.

Figure 2:
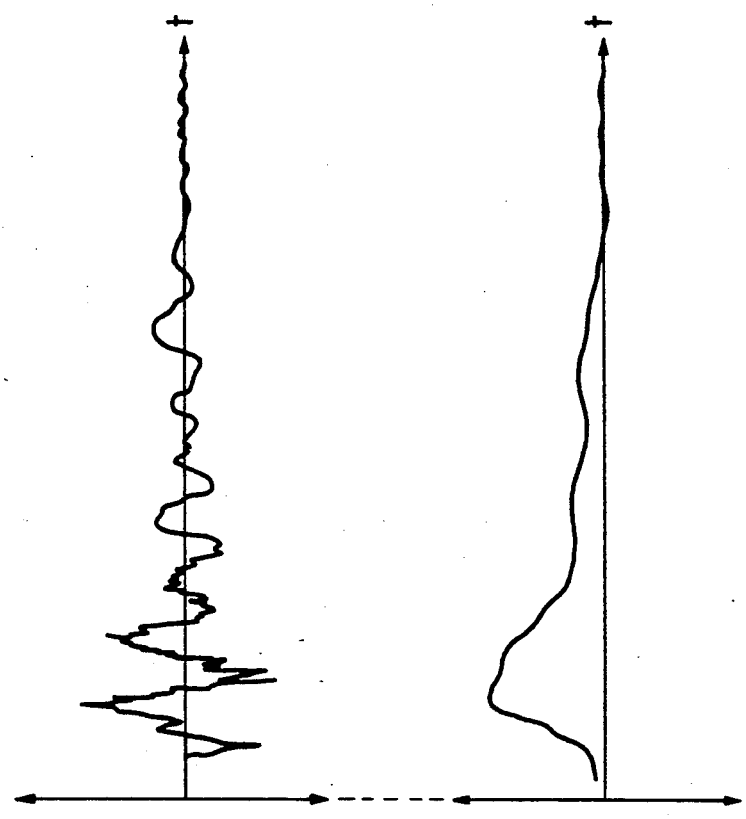
FIGS. 2A and 2B are signal waveform charts explaining operations of the oscillation degree measuring apparatus shown in FIG. 1.

The signals penetrating the band pass filter 6 form, for example, a damped oscillation wave form shown in FIG. 2A.

Then, in order to express the amplitude of the damped oscillations shown in FIG. 2A as a typical numerical value, an envelope of the damped oscillations is found by the smoothing circuit 7 as shown in FIG. 2B. By operating the A/D converter 8 a plurality of times every time a predetermined time passes according to the control of the control device 10, damped envelope signals are measured. An average value of a plurality of measurement data obtained by the A/D converter 8 is found by the data processing device 9, and the average value or a value obtained by multiplying the average value by a predetermined coefficient is displayed in the display means 11 as a measurement value of the degree of oscillation.

According to such a measurement of the degree of oscillation, even if the oscillation amplitude of the object 12, immediately after a shock is applied to the object 12, is constant, when the object is sufficiently fixed, the oscillation amplitude is promptly damped. Therefore, the measured degree of oscillation is a small value. On the other hand, if the fixing state of the object 12 is insufficient, since the oscillation is slowly damped, the measured degree of oscillation is a large value. It is possible to aptly and objectively evaluate the fixing state of the object to be measured based on the degree of oscillation obtained as these measurement values.

In an actual measurement, since a measurer has the ultrasonic explorer 4 including the ultrasonic transmitting members 3A and 3B in his hand, it is feared that an incorrect measurement is performed due to the movement of his hand or the like. Therefore, it is necessary to perform a series of measurement processes from the excitation of the ultrasonic oscillations by the pulse voltage generator 1 to the calculation of an average value by the data processing device 9 a plurality of times so as to find the average value. It is preferable that the measurements be repeated many times within a period when the measurer can stably have the ultrasonic explorer 4.

An average value of the degree of oscillation obtained in a plurality of measurements is found by the data processing device 9, a final measurement value is determined and displayed in the display device 11. In order to make the final measurement value a plain value, a process of, for example, multiplying the measurement value by a predetermined numeral, may be performed by the data processing device 9. Furthermore, if the values obtained in a plurality of measurements greatly differ, it may be judged that the influence of the movement of the ultrasonic explorer cannot be eliminated and the judgement result may be displayed.

Figure 3:
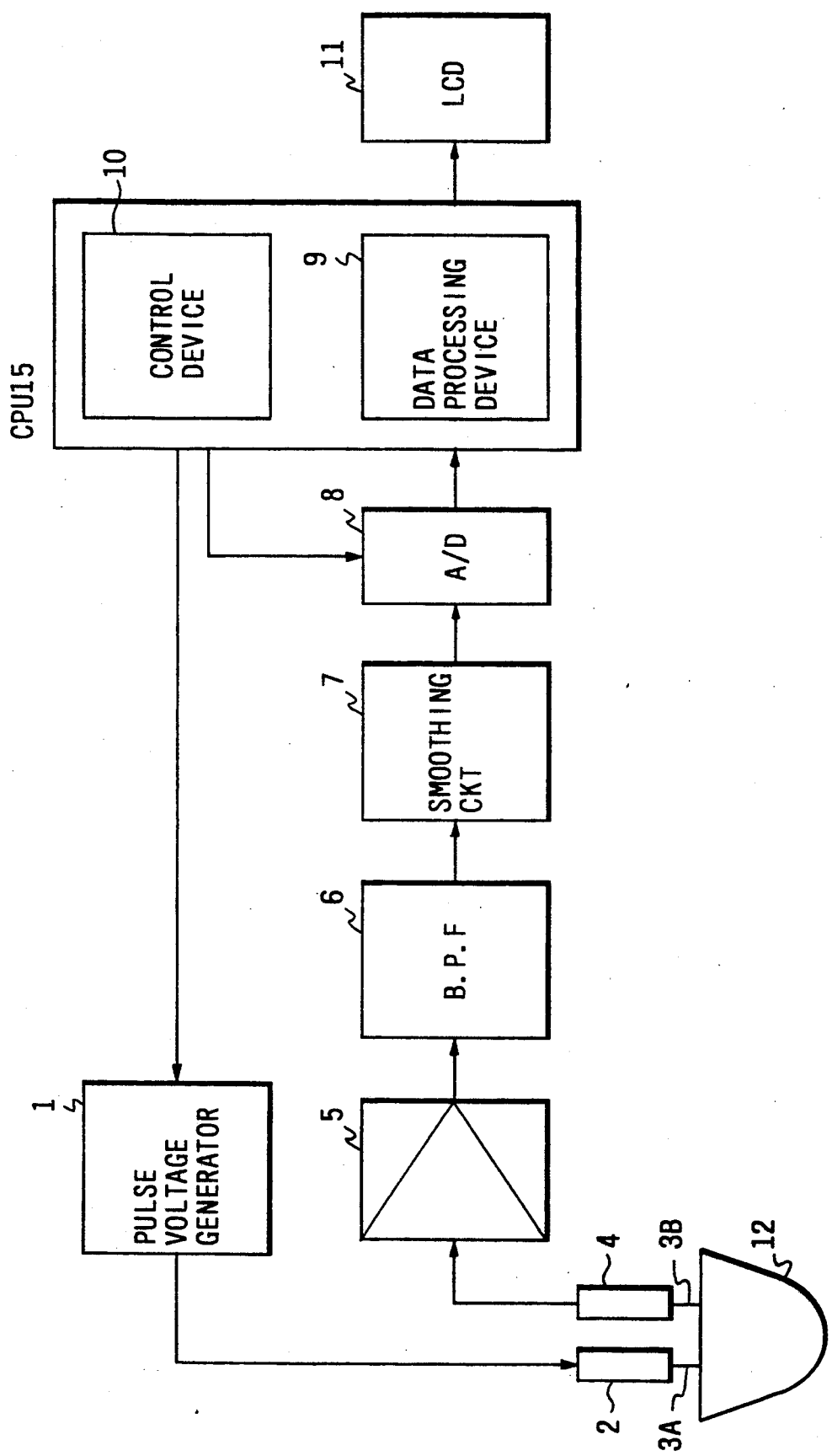
FIG. 3 is a block diagram schematically showing the composition of a more detailed embodiment of the present invention.

FIG. 3 is a block diagram of a more detailed embodiment of the present invention.

Referring to FIG. 3, a pulse voltage generator 1 repeatedly generates rectangular pulse voltage having the pulse width of 10 $\mu$sec and the amplitude of 2 to 10 V every 1 msec as shown in FIG. 4A.

The pulse voltages from the pulse voltage generator 1 are converted into ultrasonic oscillations by an ultrasonic oscillator 2 and excite resonant oscillations in a dental implant 12 as an object to be measured through one oscillation transmitting member 3A. The ultrasonic oscillator 2 to be used is, for example, a piezoelectric element of 3 mm in diameter with a stainless rod of 1 mm in diameter and approximately 30 mm in length as the oscillation transmitting member 3A attached thereto.

The oscillations excited in the implant 12 are transmitted through the other oscillation transmitting member 3B and converted into electrical signals by an ultrasonic explorer 4. The ultrasonic explorer 4 to be used is, like the ultrasonic oscillator 2, a piezoelectric element of 3 mm in diameter with a stainless rod of 1 mm in diameter and approximately 30 mm in length as the oscillation transmitting member 3B attached thereto.

Since the electrical signals converted by the ultrasonic explorer 4 are faint, they are amplified to, for example, 1000 times thereof by the amplifier 5. The amplified signals from the amplifier 5 are passed through, for example, a fifth-order Butterworth band pass filter 6 which allows only the element having the frequency of 10 to 20 KHz to pass therethrough. The signals passing the band pass filter 6 form a damped oscillation waveform shown in FIG. 4B and repeated every time a pulse voltage is generated.

Besides the Butterworth filter, an appropriate type of filter, such as a Chebyshev filter and an apposite Chebyshev filter, may be used as the band pass filter 6.

The output signals of the band pass filter 6 are given to a smoothing circuit 7 and the outputs of the smoothing circuit 7 form a signal waveform representing an envelope of a damped oscillation waveform shown in FIG. 4C.

In this embodiment, the signal voltage of the envelope output from the smoothing circuit 7 is converted into digital signals by operating an A/D converter 8 three times that is, 0.1 msec, 0.3 msec and 0.5 msec after the voltage is generated in response to a control signal, shown in FIG. 4D, from a control device 10 which is realized by a CPU 15, and measured. Finally, an average value of the three digital signals is calculated as the degree of oscillation by a function of the data processing device 9 which is realized by the CPU 15.

The above measurement is repeated under the control of the control device 10 of the CPU 15, for example, 640 times and an average value of the obtained 640 measurement values is calculated by the data processing device 9. A value obtained by multiplying the average measurement value, by for example, the coefficient 50, is regarded as a final measurement degree of oscillation and displayed in a display 11 using a liquid crystal panel. The coefficient 50 by which the average value of the 640 measurement values is multiplied is determined so that the degree of oscillation is 100 when a model in the worst fixing state is measured.

FIG. 5 is an operational flowchart showing measurement processes of the present invention.

When a measurement is started, the CPU 15 judges in Step S1 ("Step" is omitted hereinafter) whether or not a measuring period of 1 msec has passed. If the measuring period of 1 msec has passed, an ultrasonic transmission operation is performed in S2, a pulse voltage is generated by the pulse voltage generator 1, and oscillations are excited in the implant 12 through the ultrasonic oscillator 2 and the oscillation transmitting member 3A. After the ultrasonic transmission operation is performed in S2, it is watched in S3 whether or not 0.1 msec has passed since the oscillation was applied. When 0.1 msec has passed, received data is taken in S4. In other words, an envelope voltage of a damped oscillation obtained through the ultrasonic explorer 4, the amplifier 5, the band pass filter 6 and the smoothing circuit 7 by the operation of the A/D converter 8 is taken. Subsequently, it is judged in S5 whether or not 0.3 msec has passed and received data is similarly taken in S6. Furthermore, it is judged in S7 whether or not 0.5 msec has passed and received data is taken in S8 and three received data are obtained. An average value of the three received data is calculated in S8 and stored in a memory, and it is judged in S8 whether or not the number N of measurements reaches 640. If the number is less than 640, the increment is performed so that N=N+1 in S10 and a measurement operation is repeated every 1 msec returning to S1.

If the number reaches 640, an average value is calculated by dividing the sum total of 640 average measurement values by 640 in S11, the degree of oscillation is found by multiplying the average value by the coefficient 50, and finally, the numeral value is displayed in the display device in S13 and a series of processes are completed.

Although the measured value of the degree of oscillation is visually displayed in the display device 11 in the above embodiment, for example, the value may be indicated by an auditory information means, recording device or the combination thereof.

The control device 10 realized by the CPU 15 not only controls the processing of the measurement results, but also can infer optimal transmitting ultrasonic waves from the measurement results and control the pulse voltage generator 1.

Clinical examples of the measurement of the degree of oscillation (of a dental implant) according to the present invention will now be described.

When the degree of oscillation of the implants was measured according to the present invention 3 to 4 months after the implants had been buried, an example in which the implant fell away was found among the examples whose degrees of oscillation were more than 30. Furthermore, in an example, since the degree of oscillation of one implant was high, that is, approximately 40 when it was buried, the implant was removed and another implant was buried. The degree of oscillation of the new implant was less than 20 and the subsequent progress thereof has been satisfactory.

An experimental example of a model will be described. When the fixing state of a dental implant in a model was slightly changed, the measurement value changed in accordance with the fixing state, and it was revealed that the displayed degree of oscillation increased as the fixing state got worse. Furthermore, when clinical tests and experiments were repeated, it was revealed that there was a certain correspondence between the displayed degree of oscillation and the fixing state.

An object whose degree of oscillation is measured according to the present invention is not limited to a dental implant. For example, when two kinds of stainless screws (Screw A: 6 mm in diameter, 30 mm is length and 7 g in mass, Screw B: 3 mm in diameter, 6.5 mm in length and 0.6 g in mass) were screwed into holes of an apparatus having the mass of approximately 1 kg, the degree of oscillation of the screw A was 2 when the screw A was tightened and 5 when it was loosened. The degree of oscillation of the screw B was 20 when the screw B was tightened and 50 when it was loosened. Thus, the degree of oscillation varied in accordance with the degree of tightness of the screws.

These clinical examples and the model experiments prove that a value of the degree of oscillation measured according to the present invention can be thought of as a value of physical quantity which expresses the fixing state of an object properly and objectively.

As described above, the apparatus of the present invention first enables the measurement of the fixing state of a dental implant and so on as the degree of oscillation and the simple and precise judgement and evaluation of the fixing state of an object.

What is claimed is:

1. An oscillation degree measuring apparatus for measuring the fixing state of an object, comprising:
   exciting means, including an ultrasonic wave generator, for applying a shock by ultrasonic waves to the object and exciting oscillations;
   oscillation detection means for detecting the oscillations of the object and converting the oscillations into electrical signals;
   amplifying means for extracting a signal element of a predetermined frequency band including a resonant frequency of the object from the detected oscillations obtained from said oscillation detection means and amplifying the signal element;
   smoothing means for smoothing the signals amplified by said amplifying means;
   A/D converter means for converting the signals smoothed by said smoothing means into digital signals;
   control means for operating said A/D converter means a plurality of times every time a predetermined time passes; and
   data processing means for finding an average value of a plurality of digital signals obtained by said A/D converter means and calculating the degree of oscillation based on the average value.

2. An oscillation degree measuring apparatus, according to claim 1, wherein said exciting means includes a pulse voltage generator for repeatedly generating a pulse voltage in response to a timing signal from said control means, said ultrasonic wave generator being an ultrasonic oscillator including a piezoelectric element for converting the pulse voltage from said pulse voltage generator into ultrasonic oscillations, and an oscillation transmission member in contact with the object for transmitting the ultrasonic oscillations to the object so as to excite a resonant oscillation.

3. An oscillation degree measuring apparatus according to claim 1, wherein said oscillation detection means includes an ultrasonic explorer including a piezoelectric element for converting the oscillations excited in the object into electrical signals, and an oscillation transmission member in contact with the object for transmitting the oscillations of the object to said ultrasonic explorer.

4. An oscillation degree measuring apparatus according to claim 1, further comprising display means, the display means displaying the degree of oscillation calculated by said data processing means in a numerical value.

* * * * *